United States Patent [19]

Marcoux et al.

[11] Patent Number: 4,536,506
[45] Date of Patent: Aug. 20, 1985

[54] INSECTICIDAL AND ACARICIDAL COMBINATION CONTAINING A PYRETHROID

[75] Inventors: Bernard Marcoux, St. Etienne; Jean-Noël Bridon, Trevous, both of France

[73] Assignee: Rhone-Poulenc Agrochimie, Lyons, France

[21] Appl. No.: 443,557

[22] Filed: Nov. 22, 1982

[30] Foreign Application Priority Data

Dec. 1, 1981 [FR] France ............... 81 22611

[51] Int. Cl.³ .......................... A01N 43/40
[52] U.S. Cl. ..................... 514/342; 514/521; 514/531
[58] Field of Search ........................ 424/263

[56] References Cited

U.S. PATENT DOCUMENTS 4,194,001 3/1980 Ruscoe et al. ............... 424/305

FOREIGN PATENT DOCUMENTS 2135287 12/1972 France .

Primary Examiner—Leonard Schenkman
Assistant Examiner—J. Lipovsky
Attorney, Agent, or Firm—Burns, Doane, Swecker & Mathis

[57] ABSTRACT

The invention relates to insecticidal and acaricidal compositions, containing, as the active ingredient, a combination based on N,N,4-trimethyl-2-(pyrid-3-yl)-thiazole-5-carboxamide (compound A) and on a pyrethroid (compound B) of the formula:

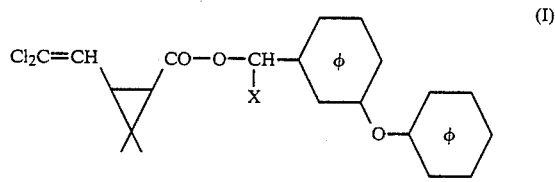

(I)

in which X represents a hydrogen atom or the cyano radical.

These compositions can be used for the protective treatment of plants, in particular cotton plants.

5 Claims, 1 Drawing Figure

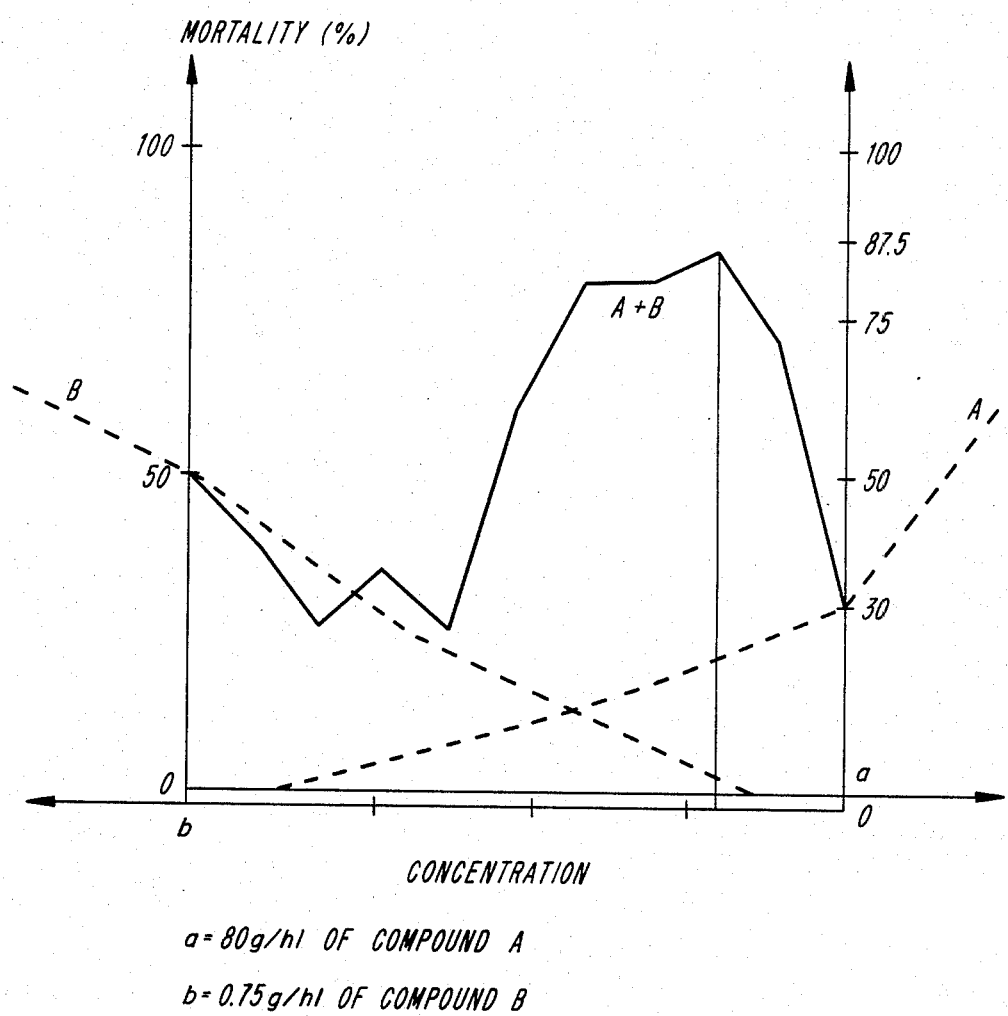

INSECTICIDAL AND ACARICIDAL COMBINATION CONTAINING A PYRETHROID

The present invention relates to insecticidal and acaricidal compositions containing, as the active ingredient, a combination comprising N,N,4-trimethyl-2-(pyrid-3-yl)-thiazole-5-carboxamide and a pyrethroid corresponding to the formula (I):

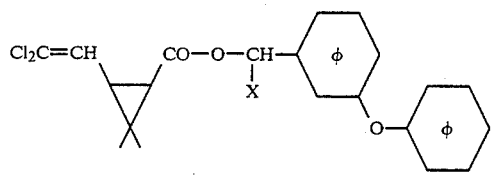

in which X represents a hydrogen atom or the cyano radical.

The invention also relates to a process for the protective treatment of plants, in particular cotton plants, by means of compositions containing this combination of active ingredients.

For the purpose of the present text, the word "combination" will denote not only ready-to-use combinations (i.e. combinations prepared beforehand and intended for use after dilution), but also mixtures of the active ingredients prepared for immediate use (i.e. prepared just before application to the crops in question).

N,N,4-Trimethyl-2-(pyrid-3-yl)-thiazole-5-carboxamide is the active ingredient of the formula (II):

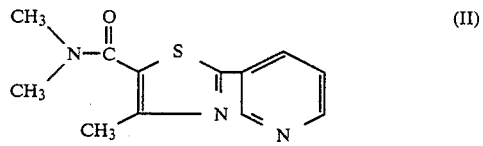

described in French Patent Application No. 2,135,287. It has a good insecticidal activity against insects of the order of the Hemiptera and more particularly, in this order, against insects of the families Aphididae (aphids, greenflies and plant lice), Psyllidae (jumping plant lice or suckers) and Aleyrodidae (whiteflies).

Pyrethroids corresponding of the formula (I) which may be mentioned are cypermethrin and permethrin, the chemical names of which are respectively: (±)-α-cyano-3-phenoxybenzyl-(±)-cis,trans-3-(2,2-dichlorovinyl)-2,2-dimethyl-cyclopropanecarboxylate and 3-phenoxybenzyl-(+)-cis,trans-3-(2,2-dichlorovinyl)-2,2-dimethyl-cyclopropanecarboxylate.

It has now been found that certain combinations of the active ingredient of the formula (I) with that of the formula (II) unexpectedly have a mutually enhanced insecticidal activity against certain insects of the family of the Aleyrodidae, which is very much greater than could be predicted by summation of the activities of the two active ingredients considered in isolation; it is this finding that forms the subject of the present invention.

The invention relates more particularly to the compositions comprising from 0.01 to 20 parts by weight of a pyrethroid according to the formula (I) per 100 parts by weight of N,N,4-trimethyl-2-(pyrid-3-yl)-thiazole-5-carboxamide.

Preferably, the compositions according to the invention comprise from 0.1 to 15 parts by weight of a pyrethroid according to the formula (I) per 100 parts by weight of N,N,4-trimethyl-2-(pyrid-3-yl)-thiazole-5-carboxamide.

Preferably, the pyrethroid used in this combination is cypermethrin.

The proportion of active ingredient (i.e. the combined proportion of the two active ingredients) in the compositions according to the invention is usually between 0.001 and 95% by weight.

The invention therefore also relates to the insecticidal and acaricidal compositions comprising, as the active ingredient, from 0.001% to 95% by weight of the combination defined above, and also containing a liquid or solid inert carrier which is acceptable in agriculture, and/or one or more surface-active agents which are also acceptable in agriculture.

These compositions according to the invention can also contain all kinds of other ingredients, such as e.g. protective colloids, adhesives, thickeners, thixotropic agents, penetrating agents, stabilisers, sequestering agents and the like, and also other known active ingredients having pesticidal properties (in particular insecticides or fungicides), properties which promote plant growth (in particular fertilisers) or properties which regulate plant growth. More generally, the synergic combination according to the invention can be used in association with any of the solid or liquid additives corresponding to the usual formulation techniques.

The invention also relates to a process for the protective treatment of plants in order to combat depreditatory or ravaging insects or mites. It relates more particularly to a process for the treatment of cotton plants in order to combat their depredators and ravagers, in particular Lepidoptera and Hemiptera, which comprises applying, to the said plants or in their vicinity, an effective amount of a composition containing, as the active ingredient, a combination of N,N,4-trimethyl-2-(pyrid-3-yl)-thiazole-5-carboxamide and of a pyrethroid corresponding to the formula (I), the said combination advantageously containing from 0.01 to 20 parts by weight of pyrethroid per 100 parts by weight of the other ingredient, but preferably from 0.1 to 15 parts of pyrethroid per 100 parts by weight of N,N,4-trimethyl-2-(pyrid-3-yl)thiazole-5-carboxamide. The pyrethroid is preferably cypermethrin.

Advantageously, the treatment according to the invention is carried out using a composition whose constitution and application dose are such that: the N,N,4-trimethyl-2-(pyrid-3-yl)-thiazole-5-carboxamide is applied at a rate of 50 g to 1,000 g/ha and preferably at a rate of 250 g/ha to 500 g/ha, and the pyrethroid of the formula (I) (preferably cypermethrin) is applied at a rate of 0.1 g/ha to 100 g/ha and preferably at a rate of 1 g/ha to 10 g/ha.

The example below illustrates the invention without however limiting it.

EXAMPLE 1

Insecticidal activity on adult aleurodes (greenhouse white fly) (*Trialeurodes vaporariorum*) of the family of the Aleyrodidae.

First, the insecticidal activity of the two active ingredients is evaluated separately.

To do this, aqueous dispersions of each of the two active ingredients are prepared. These dispersions are then diluted with distilled water so as to give aqueous dispersions of each of the active ingredients having different concentrations of active ingredient.

Bean plants of the Contender variety, cultivated in a greenhouse, are sprayed with each of the resulting dispersions until dripping wet.

After drying, one leaf is removed from each plant and placed in a Petri dish. The petiole of the leaf is enveloped in a piece of damp cotton-wool, thus ensuring the survival of the leaf.

Two Petri dishes are used for each concentration of active ingredient so as to repeat the experiment. 50 adult aleurodes are introduced into each of the dishes.

The dishes are kept closed in a laboratory at 25° C., in ambient light, with illumination for 16 hours out of 24 hours, under 70% relative humidity.

48 hours after the introduction of the aleurodes, the number of dead aleurodes is counted and the percentage mortality is thus established, this being the number of dead aleurodes relative to the total number of aleurodes introduced, expressed as the average of the two experiments.

The results are as follows:

| Dose, g/hl | % mortality |
|---|---|
| N,N,4-Trimethyl-2-(pyrid-3-yl)-thiazole-5-carboxamide | |
| 1 | 0% |
| 10 | 0% |
| 50 | 15% |
| 100 | 65% |
| 500 | 85% |
| Cypermethrin: | |
| 0.1 | 0% |
| 0.5 | 25% |
| 1 | 65% |
| 2.5 | 100% |
| 5 | 100% |

From these experiments, the doses a and b resulting in a percentage mortality of the order of 50% are determined for each of these compounds:

N,N,4-trimethyl-2-(pyrid-3-yl)-thiazole-5-carboxamide: a=80 g/hl cypermethrin: b=0.75 g/hl.

Aqueous dispersions containing mixtures of the two active ingredients are now prepared by varying the respective proportions of each of the active ingredients from 0.9a+0.1b to 0.1a+0.9b, as indicated below, and the percentage mortality is determined by the method described above. In this experiment, each of the two active ingredients is also tested at the dose "a" and at the dose "b" respectively.

Hereafter, the N,N,4-trimethyl-2-(pyrid-3-yl)-thiazole-5-carboxamide will be designated by compound "A" and the cypermethrin will be designated by compound "B". The results are as follows:

| Composition of the mixture | Percentage mortality |
|---|---|
| a + 0 b | 30% |
| 0.9 a + 0.1 b | 70% |
| 0.8 a + 0.2 b | 85% |
| 0.7 a + 0.3 b | 80% |
| 0.6 a + 0.4 b | 80% |
| 0.5 a + 0.5 b | 60% |
| 0.4 a + 0.6 b | 25% |
| 0.3 a + 0.7 b | 35% |
| 0.2 a + 0.8 b | 25% |
| 0.1 a + 0.9 b | 40% |
| 0 a + b | 50% | a = 80 g/hl of N,N,4-trimethyl-2-(pyrid-3-yl)-thiazole-5-carboxamide
b = 0.75 g/hl of cypermethrin.

These results are reported in the attached figure, which indicates, in a solid line, the results obtained with the combination of the two active ingredients, and, in broken lines, the results obtained with each of the active ingredients tested in isolation. It will be observed from this figure that the percentage mortality obtained with the mixture is considerably greater than the sum of the percentage mortalities of the two active ingredients tested in isolation at the same concentration as in the mixture, when the proportion of compound A in the mixture is between 0.45a and a and the proportion of compound b is between 0.55b and 0. Thus, there is synergy between the two active ingredients. This synergy is very strong when the proportion of compound A in the mixture is between 0.5a and 0.9a.

The compositions according to the invention or the compositions which can be used in the process of the invention, according to what has been described above, usually comprise from 0.001 to 95% (by weight) of the combination of active ingredients according to the invention (i.e. of the combination of pyrethroid plus N,N,4-trimethyl-2-(pyrid-3-yl)-thiazole-5-carboxamide). As regards the compositions modified for storage and transportation, they advantageously contain from 10 to 95% by weight of this combination of active ingredients.

According to what has already been stated, the compositions according to the invention generally contain at least one carrier and, if appropriate, at least one surface-active agent in addition to the combination of active ingredients according to the invention.

In the present account, the term "carrier" denotes an organic or inorganic, natural or synthetic material with which the active ingredients are associated in order to facilitate their application to the plant, to seeds or to the soil. This carrier is therefore generally inert and must be acceptable in agriculture, in particular to the plant treated. The carrier can be solid (clays, natural or synthetic silicates, silica, resins, waxes, solid fertilisers or the like) or liquid (water, alcohols, ketones, petroleum fractions, aromatic or paraffinic hydrocarbons, chlorohydrocarbons, liquefied gases or the like).

The surface-active agent can be an emulsifying, dispersing or wetting agent of ionic or non-ionic type. Examples which may be mentioned are salts of polyacrylic acids, salts of lignosulphonic acid, salts of phenolsulphonic or naphthalenesulphonic acids, polycondensates of ethylene oxide with fatty alcohols, fatty acids or fatty amines, substituted phenols (in particular alkylphenols or arylphenols), salts of sulphosuccinic acid esters, taurine derivatives (in particular alkyl-taurates), and phosphoric acid esters of condensates of ethylene oxide with alcohols or phenols. The presence of at least one surface-active agent is generally essential if the inert carrier is not soluble in water and if the vehicle of application is water.

The compositions according to the invention can be in a fairly wide variety of solid or liquid forms.

As forms of solid compositions, there may be mentioned dusting or sprinkling powders (with an active ingredient content which can range up to 90%).

As forms of liquid compositions or compositions which are to be made up into liquid compositions on application, there may be mentioned solutions, in particular water-soluble concentrates, emulsifiable concentrates, emulsions, suspension concentrates, aerosols, wettable powders (or spraying powders) and pastes.

The emulsifiable or soluble concentrates most frequently comprise 10 to 80% by weight of the combination of active ingredients, and the emulsions or solutions which are ready for application contain 0.001 to 20% by weight of the combination of active ingredients. In addition to the solvent, and where necessary, the emulsifiable concentrates can contain 2 to 20% by weight of suitable additives, such as stabilisers, surface-active agents, penetrating agents, corrosion inhibitors, dyestuffs and adhesives. The compositions of a few concentrates are now given as examples. Hereafter, A and B have the same meanings as above:

| combination of the active ingredients (A/B = 2.4) | 142 g/l |
|---|---|
| calcium alkylarylsulphonate | 30 g/l |
| 10:1 ethylene oxide/alkylphenol condensate | 50 g/l |
| cyclohexanone | 200 g/l |
| N,N—dimethylformamide | 200 g/l |
| aromatic solvent (petroleum cut) q.s. | 1 liter |

The composition of another emulsifiable concentrate according to the invention is now given as an example:

| combination of the active ingredients (A/B = 4.5) | 220 g/l |
|---|---|
| calcium alkylarylsulphonate | 30 g/l |
| 10:1 ethylene oxide/alkylphenol condensate | 50 g/l |
| N,N—dimethylformamide | 200 g/l |
| aromatic solvent (petroleum cut) q.s. | 1 liter |

Starting from these concentrates, emulsions of any desired concentration, which are particularly suitable for application to the leaves, can be obtained by dilution with water.

The wettable powders (or spraying powders) are usually prepared so as to contain 20 to 95% of active ingredient, and they usually contain, in addition to the solid carrier, from 0 to 5% of a wetting agent, from 3 to 10% of a dispersing agent and, where necessary, from 0 to 10% of one or more stabilisers and/or other additives, such as penetrating agents, adhesives, anti-caking agents dyestuffs and the like.

Various compositions of wettable powders are now given as examples:

| combination of active ingredients (A/B = 10) | 50% |
|---|---|
| calcium lignosulphonate (deflocculant) | 5% |
| calcium alkylarylsulphonate (anionic wetting agent) | 1% |
| anti-caking silica | 5% |
| kaolin (filler) | 39% |

Another composition of a spraying powder, this time of 70% strength, uses the following constituents:

| combination of the active ingredients (A/B = 100) | 700 g |
|---|---|
| sodium dibutylnaphthylsulphonate | 50 g |
| 3:2:1 naphthalenesulphonic acid/phenolsulphonic acid/formaldehyde condensate | 30 g |
| kaolin | 100 g |
| anti-caking silica | 50 g |
| Champagne chalk | 70 g |

Another composition of a spraying powder, this time of 40% strength, uses the following constituents:

| combination of the active ingredients (A/B = 1,000) | 400 g |
|---|---|
| sodium lignosulphonate | 50 g |
| sodium dibutylnaphthalenesulphonate | 10 g |
| silica | 540 g |

Another composition of a spraying powder, this time of 25% strength, uses the following constituents:

| combination of the active ingredients (A/B = 6.66) | 250 g |
|---|---|
| calcium lignosulphonate | 45 g |
| mixture of equal parts by weight of Champagne chalk and hydroxyethylcellulose | 19 g |
| sodium dibutylnaphthalenesulphonate | 15 g |
| silica | 195 g |
| Champagne chalk | 195 g |
| kaolin | 281 g |

Another composition of a spraying powder, this time of 10% strength, uses the following constituents:

| combination of the active ingredients (A/B = 200) | 100 g |
|---|---|
| mixture of sodium salts of saturated fatty acid sulphates | 30 g |
| naphthalenesulphonic acid/formaldehyde condensate | 820 g |

To obtain these spraying powders or wettable powders, the active ingredients are intimately mixed with the additional substances in suitable mixers, and the mixture is ground in mills or other suitable grinders. This gives spraying powders of advantageous wettability and suspendability; they can be suspended in water at any desired concentration, and this suspension can be used very advantageously, in particular for application to the leaves of the plants.

In place of the wettable powders, it is possible to produce pastes. The conditions and modes of production and use of these pastes are similar to those of the wettable powders or spraying powders.

As N,N,4-trimethyl-2-(pyrid-3-yl)-thiazole-5-carboxamide is very soluble in water, the compositions according to the invention can also be prepared in the form of aqueous compositions. To do this, an aqueous solution of N,N,4-trimethyl-2-(pyrid-3-yl)-thiazole-5-carboxamide is prepared first and the pyrethroid, i.e. cypermethrin or permethrin, is permanently emulsified therein.

As already stated, the aqueous dispersions and aqueous emulsions, e.g. compositions obtained by diluting, with water, a wettable powder or an emulsifiable concentrate according to the invention, are included in the general scope of the compositions which can be used in the present invention. The emulsions can be of the water-in-oil or oil-in-water type and they can have a thick consistency, such as that of a "mayonnaise".

For a so-called ultra-low volume (ULV) application, with spraying as very fine droplets, solutions of the two active ingredients are prepared in suitable solvents and these solutions are applied at a rate of about 1 to 5 liters/hectare. The composition of a ULV solution according to the invention is now given as an example:

| combination of the active ingredients (A/B = 10) | 110 g/l |
| aromatic solvent (petroleum cut) | 400 g/l |
| cyclohexanone | 100 g/l |
| N,N—dimethylformamide q.s. | 1 liter |

We claim:

1. An insecticidal composition effective against aleurodes comprising a combination of N,N,4-trimethyl-2-(pyrid-3-yl)-thiazole-5-carboxamide and cypermethrin, said cypermethrin being present in an amount ranging from about 0.1 to about 1 parts by weight per 100 parts by weight of said combination.

2. A composition according to claim 1, which comprises from 0.001% to 95% by weight of the insecticidal combination and at least one of an inert carrier and a surface active agent.

3. A composition of matter according to claim 1 further including an insecticidally acceptable carrier thereof.

4. A process for the protective treatment of plants to combat aleurode pests which comprises applying to said plants, an insecticidally effective amount of a composition according to claim 1.

5. A process according to claim 4 wherein the N,N,4-trimethyl-2-pyrid-3-yl)-thiazole-5-carboxamide component of the composition is applied at a rate of about 50 g/ha to about 1000 g/ha.

* * * * *